United States Patent
German et al.

(10) Patent No.: US 6,703,220 B1
(45) Date of Patent: Mar. 9, 2004

(54) HUMAN NEUROGENIN 3-ENCODING NUCLEOTIDE SEQUENCES

(75) Inventors: Michael S. German, San Francisco, CA (US); Joseph Lin, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/535,145

(22) Filed: Mar. 24, 2000

Related U.S. Application Data

(60) Provisional application No. 60/128,180, filed on Apr. 6, 1999.

(51) Int. Cl.$^7$ .................. C12N 15/12; C12N 15/63; C12N 15/85
(52) U.S. Cl. .................. 435/69.1; 435/325; 435/320.1; 435/252.3; 536/23.5; 536/23.1
(58) Field of Search .................. 536/23.5, 23.1; 435/69.1, 325, 320.1, 252.3

(56) References Cited

U.S. PATENT DOCUMENTS 5,795,723 A    8/1998  Tapscott et al. .............. 436/6

FOREIGN PATENT DOCUMENTS

| WO | WO 98/13491 | 4/1998 |
| WO | WO 00/09676 | 2/2000 |

OTHER PUBLICATIONS

Ravassard et al. J. Neuroscience Research 48: 146–158, 1997.*
Ravassard et al., Gen Bank Accession No. AJ133776, Mar. 16, 1999.*
Rudinger In "Peptide Hormones" (Ed. J.A. Parsons) University Park Press, Baltimore, pp. 1–7, 1976.*
Skolnick et al. Trends in Biotech. 18: 34–39, 2000.*
Stratagene Product Catalog, Catalog #300388, LaJolla, CA pp 62, 1991.*
Sambrook et al. "Molecular Cloning" (Second Edition) Cold Spring Harbor Laboratory Press, Cold Spring Harbor NY pp. 11.46, 1989.*
Sommer, et al., "*neurogenins*, a Novel family of atonal–Related bHLH Transcription Factors, Are Putative Mammalian Neuronal Determination Genes That Reveal Progenitor Cell Heterogeneity in the Developing CNS and PNS," *Molecular and Cellular Neuroscience* 8:221–241 (1996).
Sommer et al. GenBank Accession No. U76208, deposited Feb. 5, 1997.
Car et al. GenBank Accession No. Y09167, deposited Nov. 14, 1997.
Ravassard et al. GenBank Accession No. Y10619, deposited May 6, 1997.
Huang et al., "Regulation of the Pancreatic Islet–Specific Gene BETA2 (neuroD) by Neurogenin 3", Molecular and Cellular Biology, 2000, p. 3292–3307, vol. 20, No. 9.
Schmied et al., "Differentiation of Islet Cells in Long–Term Culture", Pancreas, 2000, p. 337–347, vol. 20, No. 4.
Xu et al., "Isolation and Characterization of the Mouse Beta2/neuroD Gene Promoter", Biochemical and Biophysical Research Communications, 1998, p. 814–818, vol. 247.

* cited by examiner

*Primary Examiner*—Gary Kunz
*Assistant Examiner*—Robert C. Hayes
(74) *Attorney, Agent, or Firm*—James S. Keddie; Carol Francis; Bozicevic, Field, & Francis LLP

(57) ABSTRACT

The present invention features a human neurogenin3 (Ngn3) polypeptide and nucleotide sequences encoding Ngn3 polypeptides. In a particular aspect, the polynucleotide is the nucleotide sequence of SEQ ID NO:1. In addition, the invention features isolated nucleic acid sequence comprising an Ngn3 promoter, as well as a polynucleotide sequences that hybridize under stringent conditions to SEQ ID NO:1. In related aspects the invention features expression vectors and host cells comprising polynucleotides that encode a human Ngn3 polypeptide. The present invention also relates to antibodies that bind specifically to a human Ngn3 polypeptide, methods for producing human Ngn3 polypeptides, methods for identifying β-cell precursor cells expressing Ngn3, methods for using the Ngn3 gene and the Ngn3 polypeptide to alter cellular differentiation in culture or in vivo to produce new β-cells to treat patients with diabetes mellitus, and identification of individuals at risk for diabetes by detecting alteration in Ngn3 coding and regulatory sequences and Ngn3 expression levels.

5 Claims, No Drawings

SEQUENCE LISTING

```
<160> NUMBER OF SEQ ID NOS: 4

<210> SEQ ID NO 1
<211> LENGTH: 5340
<212> TYPE: DNA
<213> ORGANISM: Homo sapiens
<220> FEATURE:
<221> NAME/KEY: CDS
<222> LOCATION: (3022)...(3666)
```

<223> OTHER INFORMATION: Coding sequence of human neurogenin3

<400> SEQUENCE: 1

| | | | | | |
|---|---|---|---|---|---|
| ggatccctcg | tggccagggt | tcccttcaag | gtgcttagcc | aggtcaggag | gccctagaga | 60 |
| agcatggttt | ggattttctt | tcccagacca | aaaaagctcc | aagttggttc | tctcccagtt | 120 |
| tctaacttgc | agttaaataa | atcaggcaag | gctggcctat | gaggcagaca | agtgtgaaga | 180 |
| aggagaagga | ggaggagaag | gagaaggaga | agaagaaga | aggaggagaa | gaagaagaag | 240 |
| aagaagaaga | agaagaggag | gaggaggagg | aggaggagga | agcagcagca | gcagcagcag | 300 |
| cttgaatgga | cagtggttcc | ccttgcctag | aaaatgggac | cattatttct | tttctaatct | 360 |
| gacccccaga | ctcaggactt | cctctatttt | ctgcattttg | gggtctcttg | ttttgccttg | 420 |
| aaaaaaaatg | ttttctccca | aatcaaggag | cagtagctgg | tgcaagggaa | aatctagggc | 480 |
| taggagtctt | aagatatgac | ttctatgtgg | ttctgataga | acttgctggg | tgaccttgag | 540 |
| agagtcactc | cccctctctg | ggccttgatt | ttttcatctt | taaagaaggc | ctcaaattcc | 600 |
| cattcttatg | agaagaagac | aagctcctag | tgagtggtga | cctaagggag | cagctgcagc | 660 |
| aaaatgctaa | cctgacagtc | ccagatggtc | cctttattgg | ttctgaccct | ggtctcaggc | 720 |
| ttcatttccc | cacagcaagg | gaaggagcct | gctcacagag | caccagctaa | gatcagcagg | 780 |
| accgcgccac | accccgccc | agtcctagag | ccccctctc | gctggttcct | gagcatacca | 840 |
| ccctcttcct | tggaggaaaa | tttgccccca | agcagcctag | gcggtaagag | gctatcacta | 900 |
| gggcagactc | acagacctac | ctcatcccct | caccccaccc | tacagtctcg | aagtcgggtc | 960 |
| ctgtcccctc | ctgcagtttc | cgggagactc | aggatatctg | gacctgctag | aaagagaagc | 1020 |
| cttcctcgcc | taaggagact | taaaccggga | tacttaaacc | tcccgcctcg | gcgtcttcct | 1080 |
| ccaggcacga | ccgggtcaag | agagagaagc | ggaagctgca | acccctcact | ctgagtgacc | 1140 |
| ggaagcagaa | gaccacggga | tgtcccaggc | ggggacaaga | ggaggggctg | ggaagaaag | 1200 |
| gagggatgat | gagttcagag | tccctttgga | aaggtttcca | gagagcgcta | ccagggacaa | 1260 |
| cccaagggc | tggggaagtc | cctgccttgt | gctctctgtg | cgatgcccga | gtgatgcaga | 1320 |
| ggcagggggc | tggagcaggt | gactgctggc | agctgctgtc | tgtctgtgat | tggaccggag | 1380 |
| gactaagggg | agaaaaagtt | tatcagcttc | tcccagtgcc | tgcacgctgt | ggtagttcaa | 1440 |
| aagacacgag | ggggaggggc | acagcagctc | tgcttcccag | cgccttggga | gactgaagtg | 1500 |
| aaaggaacgc | ttgagcccag | gagttcgaga | ccatcctggg | caacaaagca | agaccgcccc | 1560 |
| tcaccccata | caaaataaaa | atacaaataa | attagccggg | cacagtggcg | catgcctgta | 1620 |
| gtctcagcta | ctgggaaggc | tgaagtggga | ggatagcttg | agcccaggag | atcaaggctg | 1680 |
| cagtgagctg | tgattgcacc | actgcagtcc | agcctgggcg | acagaaggag | accgtttttt | 1740 |
| ggttttgttt | gttcgtttaa | aaaaaaaaag | aagcaagagc | tcactgtgaa | ctcctggttc | 1800 |
| cttcctcccc | tcctcacact | tcccagaact | cttcctgtca | cggttcctgg | ccagaacgct | 1860 |
| gggatactat | ctacaagctg | tagtaggctt | gtagtaatgg | aatgtccgct | tgaggggtcc | 1920 |
| ccgcacagcc | aaccccggcc | tctggagtgg | gatctatggg | ggtggggttc | taagcgcctc | 1980 |
| tggggagtgt | gaggtagcat | ctcagggtgt | ggcagaggct | cggacacccc | caaaaggtct | 2040 |
| gtgaatggaa | gggacatagg | caggatctct | ctcagtgatg | tccctgtct | tccaggatga | 2100 |
| agagaggcag | tgaaacacca | ggagagcagg | gcgtccttta | gaattcctgg | acccttctcc | 2160 |
| aggctgctag | tcaggacaat | gagctcgtgg | ttgtctttgc | cactatcttc | ctgtgcgatt | 2220 |
| tcagacaagc | cacctccctc | actaagccta | aatttcccca | tgtgtaacgt | gcaggcattg | 2280 |

```
tacccctagag gcatcaaagt cccctccagg acagatgcta aggaaagata ggctaggagc      2340
aaagccgtct gaggtggcct gaccagagcc acacgaggct cttctcactg ggcgaggctc      2400
tttgaggaac cgagagttgc tgggacccag cccgccctcg agagagcaaa cagagcggcg      2460
ctcccctccc ccgaccccgg cccttttgtcc ggaatccagc tgtgctgcgg gggaggagcg      2520
ggctcgcgtg cgcgggcccc agggcccggg cgctgattgg ccggtggcgc gggcagcagc      2580
cgggcaggca cgctcctggc ccgggcgaag cagataaagc gtgccaaggg gcacacgact      2640
tgctgctcag gaaatccctg cggtctcacc gccgcgcctc gagagagagc gtgacagagg      2700
cctcggaccc cattctctct tcttttctcc tttgggggctg gggcaactcc caggcggggg      2760
cgcctgcagc tcagctgaac ttggcgacca gaagcccgct gagctcccca cggccctcgc      2820
tgctcatcgc tctctattct tttgcgccgg tagaaaggta atatttggag gcctccgagg      2880
gacgggcagg ggaaagaggg atcctctgac ccagcggggg ctgggaggat ggctgttttt      2940
gttttttccc acctagcctc ggaatcgcgg actgcgccgt gacggactca aacttaccct      3000
tccctctgac cccgccgtag g atg acg cct caa ccc tcg ggt gcg ccc act        3051
                         Met Thr Pro Gln Pro Ser Gly Ala Pro Thr
                           1               5                  10 gtc caa gtg acc cgt gag acg gag cgg tcc ttc ccc aga gcc tcg gaa        3099
Val Gln Val Thr Arg Glu Thr Glu Arg Ser Phe Pro Arg Ala Ser Glu
         15                  20                  25 gac gaa gtg acc tgc ccc acg tcc gcc ccg ccc agc ccc act cgc aca        3147
Asp Glu Val Thr Cys Pro Thr Ser Ala Pro Pro Ser Pro Thr Arg Thr
             30                  35                  40 cgg ggg aac tgc gca gag gcg gaa gag gga ggc tgc cga ggg gcc ccg        3195
Arg Gly Asn Cys Ala Glu Ala Glu Glu Gly Gly Cys Arg Gly Ala Pro
     45                  50                  55 agg aag ctc cgg gca cgg cgc ggg gga cgc agc cgg cct aag agc gag        3243
Arg Lys Leu Arg Ala Arg Arg Gly Gly Arg Ser Arg Pro Lys Ser Glu
 60                  65                  70 ttg gca ctg agc aag cag cga cgg agt cgg cga aag aag gcc aac gac        3291
Leu Ala Leu Ser Lys Gln Arg Arg Ser Arg Arg Lys Lys Ala Asn Asp
 75                  80                  85                  90 cgc gag cgc aat cga atg cac aac ctc aac tcg gca ctg gac gcc ctg        3339
Arg Glu Arg Asn Arg Met His Asn Leu Asn Ser Ala Leu Asp Ala Leu
                 95                 100                 105 cgc ggt gtc ctg ccc acc ttc cca gac gac gcg aag ctc acc aag atc        3387
Arg Gly Val Leu Pro Thr Phe Pro Asp Asp Ala Lys Leu Thr Lys Ile
             110                 115                 120 gag acg ctg cgc ttc gcc cac aac tac atc tgg gcg ctg act caa acg        3435
Glu Thr Leu Arg Phe Ala His Asn Tyr Ile Trp Ala Leu Thr Gln Thr
         125                 130                 135 ctg cgc ata gcg gac cac agc ttg tac gcg ctg gag ccg ccg gcg ccg        3483
Leu Arg Ile Ala Asp His Ser Leu Tyr Ala Leu Glu Pro Pro Ala Pro
     140                 145                 150 cac tgc ggg gag ctg ggc agc cca ggc ggt tcc ccc ggg gac tgg ggg        3531
His Cys Gly Glu Leu Gly Ser Pro Gly Gly Ser Pro Gly Asp Trp Gly
155                 160                 165                 170 tcc ctc tac tcc cca gtc tcc cag gct ggc agc ctg agt ccc gcc gcg        3579
Ser Leu Tyr Ser Pro Val Ser Gln Ala Gly Ser Leu Ser Pro Ala Ala
                 175                 180                 185 tcg ctg gag gag cga ccc ggg ctg ctg ggg gcc acc tct tcc gcc tgc        3627
Ser Leu Glu Glu Arg Pro Gly Leu Leu Gly Ala Thr Ser Ser Ala Cys
             190                 195                 200 ttg agc cca ggc agt ctg gct ttc tca gat ttt ctg tga aaggacctgt        3676
Leu Ser Pro Gly Ser Leu Ala Phe Ser Asp Phe Leu
```

-continued

```
                205                 210
ctgtcgctgg gctgtgggtg ctaagggtaa gggagaggga gggagccggg agccgtagag    3736
ggtggccgac ggcggcggcc ctcaaaagca cttgttcctt ctgcttctcc ctggctgacc    3796
cctggccggc ccaggctcca cgggggcggc aggctgggtt cattccccgg ccctccgagc    3856
cgcgccaacg cacgcaaccc ttgctgctgc ccgcgcgaag tgggcattgc aaagtgcgct    3916
cattttaggc ctcctctctg ccaccacccc ataatctcat tcaaagaata ctagaatggt    3976
agcactaccc ggccggagcc gcccaccgtc ttgggtcgcc ctaccctcac tcaagtctgt    4036
ctgcctctca gtctcttacc accctcctc caatgtgatt caatccaatg tttggtctct    4096
cagcgcttac tccccttgcc ttgctccaaa gacgctgccg atctgctcta ctcccaatca    4156
ggtccgggat ttcagggcgc ctcactctgc cttaaagcca cgaaggcgac cctctgcctt    4216
ctcctcgtgc acttttcgga gccattgccc tcccggggcg gaagaccagg ctgtgaactg    4276
ggaaagcgct agcccggcca gggagcatct ccccagcctc cctgcgaact gcgcctgaaa    4336
cgtgagctgc gctgcaggtg cctggagcac cgcgcatctt ttttttttaa atctgtttgt    4396
aaattatatg atgccttttg aaatcaattt tggtacagta aaattatatg gcccctcccc    4456
tgttttacac atttgtattt attaatgaga tttcacagca gggaaaagcc tatattttgg    4516
atattagatt atttagggat tgctggatga catttaagcc aataaaaaaa aatggaccct    4576
caagaagcct tggcaagatg actccattgt gtgttgggga gaggagggcc acagtcacta    4636
cagctgagga agagcacttc tgtccaaaga gagggatgac actctttctg gaggtctggg    4696
ctagagccag ggcagattgg gtttggagag ctggaagtct tctaagtaat tattggtcca    4756 gctcccttt ttctatatag ggcaatgact cctcttattt caaagagtgg tttagaagaa    4816
agacaagcct ccaactagga caactgactc tcacttgctg gccctttccc caactccacc    4876
agcctagctt tagagcaact gttggttgca cttggggaag ggatacagta ataattcaat    4936
tgcagagtca gagtcctcgg aaacacggct gggctgggca tcctaggaat tttcccaagg    4996
tgcttagagg cctagcaaat ccctgagca tattttactc cccaggcact gaggtggctg     5056
tgtcgtgaac tccttgaact gagcagccag gagcaaagaa ggtggagcgt ctggctggaa    5116
tatccagcaa cgccccctcc ctcatcacct ggcagccttg attgaaaact tattaagaaa    5176
ctgttcaagg tttccagcca caccatgtct cttactggca aggtggaata ggactggtgc    5236
agcatgagca ctgaaatctg tcccaggagt gccagtagag caccactaca tgacttcagg    5296 gaccctagg acctcagaga atatggtcta agctgtaagg atcc                      5340
```

<210> SEQ ID NO 2
<211> LENGTH: 214
<212> TYPE: PRT
<213> ORGANISM: Homo sapiens

<400> SEQUENCE: 2

```
Met Thr Pro Gln Pro Ser Gly Ala Pro Thr Val Gln Val Thr Arg Glu
 1               5                  10                  15

Thr Glu Arg Ser Phe Pro Arg Ala Ser Glu Asp Glu Val Thr Cys Pro
            20                  25                  30

Thr Ser Ala Pro Pro Ser Pro Thr Arg Thr Arg Gly Asn Cys Ala Glu
        35                  40                  45

Ala Glu Glu Gly Gly Cys Arg Gly Ala Pro Arg Lys Leu Arg Ala Arg
    50                  55                  60

Arg Gly Gly Arg Ser Arg Pro Lys Ser Glu Leu Ala Leu Ser Lys Gln
```

-continued

```
             65                  70                  75                  80
Arg Arg Ser Arg Arg Lys Lys Ala Asn Asp Arg Glu Arg Asn Arg Met
                         85                  90                  95

His Asn Leu Asn Ser Ala Leu Asp Ala Leu Arg Gly Val Leu Pro Thr
                100                 105                 110

Phe Pro Asp Asp Ala Lys Leu Thr Lys Ile Glu Thr Leu Arg Phe Ala
            115                 120                 125

His Asn Tyr Ile Trp Ala Leu Thr Gln Thr Leu Arg Ile Ala Asp His
    130                 135                 140

Ser Leu Tyr Ala Leu Glu Pro Pro Ala Pro His Cys Gly Glu Leu Gly
145                 150                 155                 160

Ser Pro Gly Gly Ser Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
            180                 185                 190

Gly Leu Leu Gly Ala Thr Ser Ser Ala Cys Leu Ser Pro Gly Ser Leu
        195                 200                 205

Ala Phe Ser Asp Phe Leu
    210

<210> SEQ ID NO 3
<211> LENGTH: 1861
<212> TYPE: DNA
<213> ORGANISM: M. musculus
<220> FEATURE:
<221> NAME/KEY: CDS
<222> LOCATION: (1093)...(1737)

<400> SEQUENCE: 3
ggatcccaag gtgatattga acctggccaa gcaatagttt ctgagtagaa aggacttgag      60
cagggaccgt ctctggtcac tctgtcctct ttcccaggat ggagtcagtc tgtgaaacat     120
ggttgcacac acatttcctg acccaaccca tagtggcgga gagctggata gcactttgaa     180
ctaatgggcg ctcctcccag ctgccagcca agaagacact tgactccttg atcgctggtt     240
catttagaca agccgtttcc ctctctgagc aaaagaccc  catgtgtaat actcaaagaa     300
gaggccttcc ttatatatat ataggcaccc ccaaacctcc ttcatgctac caagaaaggg     360
tctggacaca tgccaaaaag aaagaggaaa aggcaaagct ctccccagcg gccggacggg     420
actcttctgg ctgggcgagg ctctttgagg aaccgagagt tgctgggact gagcccgcga     480
cgggggaggc gtggagtggg ggaacaaaca gagtgctgct cccctccccc gaccctgcc      540 ctttgtccgg aatccagctg tgctctgcgg gtgggggttg tgggggagg  agcgggctcg     600 cgtggcgcag ccctgggcc  cctccgctg  attggcccgt ggtgcaggca gcagcccggc     660
aggcacgctc ctggccgggg gcagagcaga taaagcgtgc caggggacac acgacttgca    720
tgcagctcag aaatccctct gggtctcatc actgcagcag tggtcgagta cctcctcgga    780
gcttttctac gacttccaga cgcaatttac tccaggcgag gcgcctgca  gtttagcaga    840 acttcagagg gagcagagag gctcagctat ccactgctgc ttgacactga ccctatccac    900
tgctgcttgt cactgactga cctgctgctc tctattcttt tgagtcggga gaactaggta    960
acaattcgga aactccaaag ggtggatgag gggcgcgcgg ggtgtgtgtg ggggatactc   1020
tggtcccccg tgcagtgacc tctaagtcag aggctggcac acacacacct tccattttt    1080 cccaaccgca gg atg gcg cct cat ccc ttg gat gcg ctc acc atc caa gtg  1131
              Met Ala Pro His Pro Leu Asp Ala Leu Thr Ile Gln Val
                1               5                  10
```

-continued

| | | | | | | | | | | | | | | | |
|---|---|---|---|---|---|---|---|---|---|---|---|---|---|---|---|
| tcc | cca | gag | aca | caa | caa | cct | ttt | ccc | gga | gcc | tcg | gac | cac | gaa | gtg |
| Ser | Pro | Glu | Thr | Gln | Gln | Pro | Phe | Pro | Gly | Ala | Ser | Asp | His | Glu | Val |
| | 15 | | | | 20 | | | | | 25 | | | | | |

1179 ctc agt tcc aat tcc acc cca cct agc ccc act ctc ata cct agg gac    1227
Leu Ser Ser Asn Ser Thr Pro Pro Ser Pro Thr Leu Ile Pro Arg Asp
 30              35                  40                  45 tgc tcc gaa gca gaa gtg ggt gac tgc cga ggg acc tcg agg aag ctc    1275
Cys Ser Glu Ala Glu Val Gly Asp Cys Arg Gly Thr Ser Arg Lys Leu
             50                  55                  60 cgc gcc cga cgc gga ggg cgc aac agg ccc aag agc gag ttg gca ctc    1323
Arg Ala Arg Arg Gly Gly Arg Asn Arg Pro Lys Ser Glu Leu Ala Leu
         65                  70                  75 agc aaa cag cga aga agc cgg cgc aag aag gcc aat gat cgg gag cgc    1371
Ser Lys Gln Arg Arg Ser Arg Arg Lys Lys Ala Asn Asp Arg Glu Arg
     80                  85                  90 aat cgc atg cac aac ctc aac tcg gcg ctg gat gcg ctg cgc ggt gtc    1419
Asn Arg Met His Asn Leu Asn Ser Ala Leu Asp Ala Leu Arg Gly Val
 95                 100                 105 ctg ccc acc ttc ccg gat gac gcc aaa ctt aca aag atc gag acc ctg    1467
Leu Pro Thr Phe Pro Asp Asp Ala Lys Leu Thr Lys Ile Glu Thr Leu
110             115                 120                 125 cgc ttc gcc cac aac tac atc tgg gca ctg act cag acg ctg cgc ata    1515
Arg Phe Ala His Asn Tyr Ile Trp Ala Leu Thr Gln Thr Leu Arg Ile
                130                 135                 140 gcg gac cac agc ttc tat ggc ccg gag ccc cct gtg ccc tgt gga gag    1563
Ala Asp His Ser Phe Tyr Gly Pro Glu Pro Pro Val Pro Cys Gly Glu
            145                 150                 155 ctg ggg agc ccc gga ggt ggc tcc aac ggg gac tgg ggc tct atc tac    1611
Leu Gly Ser Pro Gly Gly Gly Ser Asn Gly Asp Trp Gly Ser Ile Tyr
        160                 165                 170 tcc cca gtc tcc caa gcg ggt aac ctg agc ccc acg gcc tca ttg gag    1659
Ser Pro Val Ser Gln Ala Gly Asn Leu Ser Pro Thr Ala Ser Leu Glu
    175                 180                 185 gaa ttc cct ggc ctg cag gtg ccc agc tcc cca tcc tat ctg ctc ccg    1707
Glu Phe Pro Gly Leu Gln Val Pro Ser Ser Pro Ser Tyr Leu Leu Pro
190                 195                 200                 205 gga gca ctg gtg ttc tca gac ttc ttg tga agagacctgt ctggctctgg      1757
Gly Ala Leu Val Phe Ser Asp Phe Leu
                210 gtggtgggtg ctagtggaaa gggaggggac cagagccgtc tggagtggga ggtagtggag  1817 gctctcaagc atctcgcctc ttctggcttt cactacttgg atcc                  1861

<210> SEQ ID NO 4
<211> LENGTH: 214
<212> TYPE: PRT
<213> ORGANISM: M. musculus

<400> SEQUENCE: 4

Met Ala Pro His Pro Leu Asp Ala Leu Thr Ile Gln Val Ser Pro Glu
 1               5                  10                  15

Thr Gln Gln Pro Phe Pro Gly Ala Ser Asp His Glu Val Leu Ser Ser
             20                  25                  30

Asn Ser Thr Pro Pro Ser Pro Thr Leu Ile Pro Arg Asp Cys Ser Glu
         35                  40                  45

Ala Glu Val Gly Asp Cys Arg Gly Thr Ser Arg Lys Leu Arg Ala Arg
     50                  55                  60

Arg Gly Gly Arg Asn Arg Pro Lys Ser Glu Leu Ala Leu Ser Lys Gln
 65                  70                  75                  80

-continued

```
Arg Arg Ser Arg Arg Lys Lys Ala Asn Asp Arg Glu Arg Asn Arg Met
            85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
            115                 120                 125

His Asn Tyr Ile Trp Ala Leu Thr Gln Thr Leu Arg Ile Ala Asp His
            130                 135                 140

Ser Phe Tyr Gly Pro Glu Pro Pro Val Pro Cys Gly Glu Leu Gly Ser
145                 150                 155                 160

Pro Gly Gly Gly Ser Asn Gly Asp Trp Gly Ser Ile Tyr Ser Pro Val
                165                 170                 175

Ser Gln Ala Gly Asn Leu Ser Pro Thr Ala Ser Leu Glu Glu Phe Pro
            180                 185                 190

Gly Leu Gln Val Pro Ser Ser Pro Ser Tyr Leu Leu Pro Gly Ala Leu
            195                 200                 205

Val Phe Ser Asp Phe Leu
        210
```

HUMAN NEUROGENIN 3-ENCODING NUCLEOTIDE SEQUENCES

CROSS-REFERENCE TO RELATED APPLICATION

This applications claims the benefit of U.S. Provisional Application Serial No. 60/128,180, filed Apr. 6, 1999, which application is incorporated herein by reference.

FIELD OF THE INVENTION

The invention relates generally to the field of nucleotide sequences encoding transcription factors involved in growth and differentiation, particularly development of pancreatic islet cells.

BACKGROUND OF THE INVENTION

Diabetes mellitus is the third leading cause of death in the U.S. and the leading cause of blindness, renal failure, and amputation. Diabetes is also a major cause of premature heart attacks and stroke and accounts for 15% of U.S. health care costs. Approximately 5% of Americans, and as many as 20% of those over the age of 65, have diabetes.

Diabetes results from the failure of the β-cells in the islets of Langerhans in the endocrine pancreas to produce adequate insulin to meet metabolic needs. Diabetes is categorized into two clinical forms: Type 1 diabetes (or insulin-dependent diabetes) and Type 2 diabetes (or non-insulin-dependent diabetes). Type 1 diabetes is caused by the loss of the insulin-producing β-cells. Type 2 diabetes is a more strongly genetic disease than Type 1 (Zonana & Rimoin, 1976 N. Engl. J. Med. 295:603), usually has its onset alter in life, and accounts for approximately 90% of diabetes in the U.S. Affected individuals usually have both a decrease in the capacity of the pancreas to produce insulin and a defect in the ability to utilize the insulin (insulin resistance). Obesity causes insulin resistance, and approximately 80% of individuals with Type 2 diabetes are clinically obese (greater than 20% above ideal body weight). Unfortunately, about one-half of the people in the U.S. affected by Type 2 diabetes are unaware that they have the disease. Clinical symptoms associated with Type 2 diabetes may not become obvious until late in the disease, and the early signs are often misdiagnosed, causing a delay in treatment and increased complications. While the role of genetics in the etiology of type 2 diabetes is clear, the precise genes involved are largely unknown.

Insulin is made exclusively by the β-cells in the islets of Langerhans in the pancreas. During development, the islet cells, including the β-cells, develop from an undifferentiated precursor within the growing pancreatic bud. As the bud grows, the undifferentiated cells form into ducts, and it is these cells that function as precursors. Duct cells appear to retain the capacity to differentiate into islet cells throughout life, and when the pancreas is damaged, new islet cells form from the duct cells.

This developmental process is clinically relevant for several reasons. First, the formation of islet cells and especially β-cells is necessary in order to make insulin and control energy metabolism. If the process of β-cell development is in anyway impaired, it predisposes that individual to the later development of diabetes. Therefore genes involved in this process are candidate genes for neonatal diabetes, maturity onset diabetes of the young (MODY) or type 2 diabetes. The sequence of these genes could be used to identify individuals at risk for the development of diabetes, or to develop new pharmacological agents to prevent and treat diabetes.

Second, as discussed above, insulin production is impaired in individuals with diabetes. In type 1 diabetes the impairment is caused by the destruction of the beta-cells, while in type 2 diabetes, insulin production is intact, but inadequate. Treatment of type 1 diabetes, as well as many cases of type 2 diabetes, may involve replacement of the β-cells. While replacement of β-cells may be accomplished in several ways, the development of new β-cells from precursor cells, either in culture or in vivo in the patient, would be the most physiologic. To do this, the molecules that control beta-cell differentiation are needed.

For these reasons, the diabetes field has spent considerable effort in attempts to identify islet precursor cells, and to develop methods for differentiating beta-cells in vitro. To date this has been largely unsuccessful. The present invention addresses this problem.

Relevant Literature

A cloned fragment of mouse Ngn3 is described in Sommer et al. 1996 Mol. Cell. Neurosci. 8:221.

cDNA and amino acid sequences of murine Ngn3 and murine mammalian atonal homology 4B (MATH4B) are described at GenBank Accession Nos. U76208 and Y09167, respectively.

cDNA and amino acid sequences of the rat relax transcriptional regulator are described at GenBank Accession No. Y10619.

SUMMARY OF THE INVENTION

The present invention features a human neurogenin3 (Ngn3) polypeptide and nucleotide sequences encoding Ngn3 polypeptides. In a particular aspect, the polynucleotide is the nucleotide sequence of SEQ ID NO:1. In addition, the invention features isolated nucleic acid sequence comprising an Ngn3 promoter, as well as a polynucleotide sequences that hybridize under stringent conditions to SEQ ID NO:1. In related aspects the invention features expression vectors and host cells comprising polynucleotides that encode a human Ngn3 polypeptide. The present invention also relates to antibodies that bind specifically to a human Ngn3 polypeptide, methods for producing human Ngn3 polypeptides, methods for identifying β-cell precursor cells expressing Ngn3, methods for using the Ngn3 gene and the Ngn3 polypeptide to alter cellular differentiation in culture or in vivo to produce new β-cells to treat patients with diabetes mellitus, and identification of individuals at risk for diabetes by detecting alteration in Ngn3 coding and regulatory sequences and Ngn3 expression levels.

A primary object of the invention is to provide an isolated human Ngn3 polypeptide-encoding polynucleotide for use in expression of human Ngn3 (e.g, in a recombinant host cell) and for use in, for example, identification of human Ngn3 polypeptide binding compounds (especially those compounds that affect human Ngn3 polypeptide-mediated activity, which compounds can be used to modulate Ngn3 activity).

Another object of the invention is to provide an isolated human Ngn3 polypeptide-encoding polynucleotide for use in generation of non-human transgenic animal models for Ngn3 gene function, particularly "knock-in" Ngn3 non-human transgenic animals characterized by excess or ectopic expression of the Ngn3 gene.

These and other objects, advantages and features of the present invention will become apparent to those persons skilled in the art upon reading the details of the invention more fully set forth below.

The invention will now be described in further detail.

DETAILED DESCRIPTION OF THE INVENTION

Before the present nucleotide and polypeptide sequences are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a host cell" includes a plurality of such host cells and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

Definitions

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. a Ngn3 polypeptide-encoding polynucleotide), "polynucleotide" is meant to encompass polynucleotides that encode a polypeptide that is functionally equivalent to the recited polypeptide, e.g., polynucleotides that are degenerate variants, or polynucleotides that encode biologically active variants or fragments of the recited polypeptide, including polynucleotides having substantial sequence similarity or sequence identity relative to the sequences provided herein. Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule, but instead is meant to also encompass biologically active variants or fragments, including polypeptides having substantial sequence similarity or sequence identify relative to the amino acid sequences provided herein.

By "antisense polynucleotide" is mean a polynucleotide having a nucleotide sequence complementary to a given polynucleotide sequence (e.g, a polynucleotide sequence encoding an Ngn3 polypeptide) including polynucleotide sequences associated with the transcription or translation of the given polynucleotide sequence (e.g., a promoter of a polynucleotide encoding an Ngn3 polypeptide), where the antisense polynucleotide is capable of hybridizing to an Ngn3 polypeptide-encoding polynucleotide sequence. Of particular interest are antisense polynucleotides capable of inhibiting transcription and/or translation of an Ngn3-encoding polynucleotide either in vitro or in vivo.

"Peptide nucleic acid" as used herein refers to a molecule which comprises an oligomer to which an amino acid residue, such as lysine, and an amino group have been added. These small molecules, also designated antigene agents, stop transcript elongation by binding to their complementary (template) strand of nucleic acid (Nielsen et al 1993 Anticancer Drug Des 8:53-63).

As used herein, "Ngn3 polypeptide" refers to an amino acid sequence of a recombinant or nonrecombinant polypeptide having an amino acid sequence of i) a native Ngn3 polypeptide, ii) a biologically active fragment of an Ngn3 polypeptide, iii) biologically active polypeptide analogs of an Ngn3 polypeptide, or iv) a biologically active variant of an Ngn3 polypeptide. Ngn3 polypeptides of the invention can be obtained from any species, e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human, from any source whether natural, synthetic, semi-synthetic or recombinant. "Human Ngn3 polypeptide" refers to the amino acid sequences of isolated human Ngn3 polypeptide obtained from a human, and is meant to include all naturally-occurring allelic variants, and is not meant to limit the amino acid sequence to the complete, native amino acid sequence associated with the recited protein molecule.

As used herein, "antigenic amino acid sequence" means an amino acid sequence that, either alone or in association with a carrier molecule, can elicit an antibody response in a mammal.

A "variant" of a human Ngn3 polypeptide is defined as an amino acid sequence that is altered by one or more amino acids. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include aminoacid deletions or insertions, or both. Guidance in determining which and how many amino acid residues may be substituted, inserted or deleted without abolishing biological or immunological activity can be found using computer programs well known in the art, for example, DNAStar software.

A "deletion" is defined as a change in either amino acid or nucleotide sequence in which one or more amino acid or nucleotide residues, respectively, are absent as compared to an amino acid sequence or nucleotide sequence of a naturally occurring Ngn3 polypeptide.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring Ngn3 polypeptide.

A "substitution" results from the replacement of one or more amino acids or nucleotides by different amino acids or nucleotides, respectively as compared to an amino acid sequence or nucleotide sequence of a naturally occurring Ngn3 polypeptide.

The term "biologically active" refers to human Ngn3 polypeptide having structural, regulatory, or biochemical functions of a naturally occurring Ngn3 polypeptide. Likewise, "immunologically active" defines the capability of the natural, recombinant or synthetic human Ngn3 polypeptide, or any oligopeptide thereof, to induce a specific immune response in appropriate animals or cells and to bind with specific antibodies.

The term "derivative" as used herein refers to the chemical modification of a nucleic acid encoding a human Ngn3 polypeptide or the encoded human Ngn3 polypeptide. Illustrative of such modifications would be replacement of hydrogen by an alkyl, acyl, or amino group. A nucleic acid derivative would encode a polypeptide which retains essential biological characteristics of a natural Ngn3 polypeptide.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

"Stringency" typically occurs in a range from about Tm-5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs 1994 Dictionary of Biotechnology, Stockton Press, New York N.Y.). Amplification as carried out in the polymerase chain reaction technologies is described in Dieffenbach et al. 1995, PCR Primer, a Laboratory Manual, Cold Spring Harbor Press, Plainview N.Y.

By "transformation" is meant a permanent or transient genetic change, preferably a permanent genetic change, induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

By "construct" is meant a recombinant nucleic acid, generally recombinant DNA, that has been generated for the purpose of the expression of a specific nucleotide sequence (s), or is to be used in the construction of other recombinant nucleotide sequences.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by an Ngn3 sequence).

By "Ngn3 associated disorder" is meant a physiological condition or disease associated with altered Ngn3 function (e.g., due to aberrant Ngn3 expression or a defect in Ngn3 expression or in the Ngn3 protein). Such Ngn3 associated disorders can include, but are not necessarily limited to, disorders associated with reduced levels of insulin or the ability to utilize insulin (e.g., hyperglycemia, diabetes (e.g., Type 1 and Type 2 diabetes, and the like).

By "subject" or "patient" is meant any mammalian subject for whom diagnosis or therapy is desired, particularly humans. Other subjects may include cattle, dogs, cats, guinea pigs, rabbits, rats, mice, horses, and so on. Of particular interest are subjects having an Ngn3-associated disorder that is amenable to treatment (e.g., to mitigate symptoms associated with the disorder) by expression of either Ngn3-encoding nucleic acid in a cell of the subject (e.g., by introduction of the Ngn3-encoding nucleic acid into the subject in vivo, or by implanting Ngn3-expressing cells (e.g., β-cell precursors) or nearly developed or mature β-cells, cultured from Ngn3-expressing cells into the subject, which cells produce insulin).

The term "transgene" is used herein to describe genetic material which has been or is about to be artificially inserted into the genome of a mammalian, particularly a mammalian cell of a living animal.

By "transgenic organism" is meant a non-human organism (e.g., single-cell organisms (e.g., yeast), mammal, non-mammal (e.g., nematode or Drosophila)) having a non-endogenous (i.e., heterologous) nucleic acid sequence present as an extrachromosomal element in a portion of its cells or stably integrated into its germ line DNA.

By "transgenic animal" is meant a non-human animal, usually a mammal, having a non-endogenous (i.e. heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

A "knock-out" of a target gene means an alteration in the sequence of the gene that results in a decrease of function of the target gene, preferably such that target gene expression is undetectable or insignificant. A knock-out of an Ngn3 gene means that function of the Ngn3 gene has been substantially decreased so that Ngn3 expression is not detectable or only present at insignificant levels. "Knock-out" transgenics of the invention can be transgenic animals having a heterozygous knock-out of the Ngn3 gene or a homozygous knock-out of the Ngn3 gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of the target gene, e.g., by introduction of an additional copy of the target gene, or by operatively inserting a regulatory sequence that provides for enhanced expression of an endogenous copy of the target gene. "Knock-in" transgenics of the invention can be transgenic animals having a heterozygous knock-in of the Ngn3 gene or a homozygous knock-in of the Ngn3 gene. "Knock-ins" also encompass conditional knock-ins.

Overview of the Invention

The present invention is based upon the identification and isolation of a polynucleotide sequence encoding a human neurogenin3 (Ngn3) polypeptide, as well as the human and murine Ngn3 promoters. Accordingly, the present invention encompasses such human Ngn3 polypeptide-encoding polynucleotides, as well as human Ngn3 polypeptides encoded by such polynucleotides. Expression of Ngn3 is linked to pancreatic development. Specifically, Ngn3 expression is the earliest available marker of cells that will develop into islet cells. Because Ngn3 expression is extinguished before the cells are completely differentiated, Ngn3 uniquely marks precursor cells. The proof that these are islet cell precursors is based on three pieces of evidence: 1) Expression pattern. Ngn3 cells are seen scattered through the pancreatic duct cells, with a smaller number present adjacent to the ducts. 2) Timing. The appearance of the Ngn3-positive cells parallels the formation of new islet cells during development. 3) Ngn3-positive cells co-express other endocrine transcription factors, including the β-cell transcription factor Nkx-6.1. Nkx6.1 is known to be expressed in β-cells and β-cell precursors at this stage of pancreatic development, and the knock-out of the Nkx-6.1 gene in mice causes a specific defect in β-cell development, but no defect in the formation of other pancreatic cells (see, e.g., WO 99/05258).

The invention also encompasses the use of the polynucleotides disclosed herein to facilitate identification and isolation of polynucleotide and polypeptide sequences having homology to a human Ngn3 polypeptide of the invention. The human Ngn3 polypeptides and polynucleotides of the invention are also useful in the identification of human Ngn3 polypeptide-binding compounds, particularly human Ngn3 polypeptide-binding compounds having human Ngn3 polypeptide agonist or antagonist activity. In addition, the human Ngn3 polypeptides and polynucleotides of the invention are useful in the diagnosis, prevention and treatment of disease associated with human Ngn3 polypeptide biological activity.

The human Ngn3 polypeptide-encoding polynucleotides of the invention can also be used in the development of β-cells in culture and in vivo, as a molecular probe with which to determine the structure, location, and expression of the human Ngn3 polypeptide and related polypeptides in mammals (including humans), and to investigate potential associations between disease states or clinical disorders and defects or alterations in human Ngn3 polypeptide structure, expression, or function.

Ngn3 Nucleic Acid

The term "Ngn3 gene" is used generically to designate Ngn3 genes and their alternate forms. "Ngn3 gene" is also intended to mean the open reading frame encoding specific Ngn3 polypeptides, introns, and adjacent 5' and 3' non-coding nucleotide sequences involved in the regulation of expression, up to about 1 kb beyond the coding region, but possibly further in either direction. The DNA sequences encoding Ngn3 may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the Ngn3 polypeptide.

While other genomic Ngn3 sequences of other sources may have non-contiguous open reading frames (e.g., where introns interrupt the protein coding regions), the human genomic Ngn3 sequence has no introns interrupting the coding sequence. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where Ngn3 is expressed. The sequences of the Ngn3 promoter elements of the invention can be based on the nucleotide sequences of any species (e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human) and can be isolated or produced from any source whether natural, synthetic, semi-synthetic or recombinant.

The tissue specific expression of Ngn3 is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. 1995 Mol Med 1:194–205; Mortlock et al. 1996 Genome Res. 6:327–33; and Joulin and Richard-Foy (1995) Eur J Biochem 232:620–626.

In one embodiment, the Ngn3 promoter is used to direct expression of genes to islet cell precursors. As discussed below, Ngn3 is expressed in islet cell precursors during development of β-cells. Thus, the developmentally timed expression directed by the Ngn3 promoter can be exploited to facilitate expression of heterologous genes operably linked to the Ngn3 promoter. Exemplary genes of interest that can be expressed from the Ngn3 promoter include, but are not necessarily limited to, genes encoding growth factors or onocogenes (e.g., to expand and/or immortalize the β-cell progenitor population), marker genes (e.g., for marking the precursor cells for selection and/or tracing), reporter genes (e.g., luciferase, CAT, etc., for, e.g., identifying mechanisms for regulating the Ngn3 promoter and/or to search for bioactive agents (e.g., candidate pharmaceutical agents) that regulate the promoter), and the like.

The regulatory sequences may be used to identify cis acting sequences required for transcriptional or translational regulation of Ngn3 expression, especially in different tissues or stages of development, and to identify cis acting sequences and trans acting factors that regulate or mediate Ngn3 expression. Such transcriptional or translational control regions may be operably linked to an Ngn3 gene or other genes in order to promote expression of wild type or altered Ngn3 or other proteins of interest in cultured cells, or in embryonic, fetal or adult tissues, and for gene therapy. Ngn3 transcriptional or translational control regions can also be used to identify extracellular signal molecules that regulate Ngn3 promoter activity, and thus regulate Ngn3 expression and islet cell formation.

The nucleic acid compositions used in the subject invention may encode all or a part of the Ngn3 polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The Ngn3 gene is isolated and obtained in substantial purity, generally as other than an intact mammalian chromosome. Usually, the DNA will be obtained substantially free of other nucleic acid sequences that do not include an Ngn3 sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying homologs of Ngn3. Mammalian homologs have substantial sequence similarity to one another, i.e. at least 75%, usually at least 90%, more usually at least 95% sequence identity. Sequence similarity and sequence identity are calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. 1990 J Mol Biol 215:403–10.

Nucleic acids having sequence similarity are detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). Sequence identity may be determined by hybridization under high stringency conditions, for example, at 50° C. or higher and 0.1×SSC (15 mM saline/0.15 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, Drosophila, Caenhorabditis, etc.

The Ngn3-encoding DNA may be used to identify expression of the gene in a biological specimen. The manner in which one probes cells for the presence of particular nucleotide sequences, as genomic DNA or RNA, is well established in the literature and does not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to an Ngn3 sequence is indicative of Ngn3 gene expression in the sample.

The Ngn3 nucleic acid sequence may be modified for a number of purposes, particularly where they will be used intracellularly, for example, by being joined to a nucleic acid cleaving agent, e.g. a chelated metal ion, such as iron or chromium for cleavage of the gene; or the like.

The sequence of the Ngn3 locus, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of Ngn3 polypeptides with other polypeptides (e.g., Nkx-6.1, which is co-expressed with Ngn3), or to alter properties of the proteins that affect their function or regulation. Such modified Ngn3 sequences can be used to, for example, generate the transgenic animals.

Techniques for in vitro mutagenesis of cloned genes are known. Examples of protocols for scanning mutations may be found in Gustin et al., 1993 Biotechniques 14:22; Barany, 1985 Gene 37:111–23; Colicelli et al., 1985 Mol Gen Genet 199:537–9; and Prentki et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4.

Ngn3 Transgenic Animals

The Ngn3-encoding nucleic acids can be used to generate genetically modified non-human animals or site specific gene modifications in cell lines. The term "transgenic" is intended to encompass genetically modified animals having a deletion or other knock-out of Ngn3 gene activity, having an exogenous Ngn3 gene that is stably transmitted in the host cells, "knock-in" having altered Ngn3 gene expression, or having an exogenous Ngn3 promoter operably linked to a reporter gene. Of particular interest are homozygous and heterozygous knock-outs of Ngn3.

Transgenic animals may be made through homologous recombination, where the Ngn3 locus is altered. Alternatively, a nucleic acid construct is randomly integrated into the genome. Vectors for stable integration include plasmids, retroviruses and other animal viruses, YACs, and the like. Of interest are transgenic mammals, preferably a mammal from a genus selected from the group consisting of Mus (e.g., mice), Rattus (e.g., rats), Oryctolagus (e.g., rabbits) and Mesocricetus (e.g., hamsters). More preferably the animal is a mouse which is defective or contains some other alteration in Ngn3 gene expression or function. Without being held to theory, Ngn3 is a transcription factor that is expressed in islet cell precursors during pancreatic development, transgenic animals having altered Ngn3 gene expression will be useful models of pancreatic development.

A "knock-out" animal is genetically manipulated to substantially reduce, or eliminate endogenous Ngn3 function, preferably such that target gene expression is undetectable or insignificant. Different approaches may be used to achieve the "knock-out". A chromosomal deletion of all or part of the native Ngn3 homolog may be induced. Deletions of the non-coding regions, particularly the promoter region, 3' regulatory sequences, enhancers, or deletions of gene that activate expression of the Ngn3 genes. A functional knock-out may also be achieved by the introduction of an anti-sense construct that blocks expression of the native Ngn3 gene (for example, see Li and Cohen (1996) Cell 85:319–329).

Conditional knock-outs of Ngn3 gene function can also be generated. Conditional a knock-outs are transgenic animals that exhibit a defect in Ngn3 gene function upon exposure of the animal to a substance that promotes target gene alteration, introduction of an enzyme that promotes recombination at the target gene site (e.g., Cre in the Cre-loxP system), or other method for directing the target gene alteration.

For example, a transgenic animal having a conditional knock-out of Ngn3 gene function can be produced using the Cre-loxP recombination system (see, e.g., Kilby et al. 1993 Trends Genet 9:413–421). Cre is an enzyme that excises the DNA between two recognition sequences, termed loxP. This system can be used in a variety of ways to create conditional knock-outs of Ngn3. For example, two independent transgenic mice can be produced: one transgenic for an Ngn3 sequence flanked by loxp sites and a second transgenic for Cre. The Cre transgene can be under the control of an inducible or developmentally regulated promoter (Gu et al. 1993 Cell 73:1155–1164; Gu et al. 1994 Science 265:103–106), or under control of a tissue-specific or cell type-specific promoter (e.g., a pancreas-specific promoter or brain tissue-specific promoter). The Ngn3 transgenic is then crossed with the Cre transgenic to produce progeny deficient for the Ngn3 gene only in those cells that expressed Cre during development.

Transgenic animals may be made having an exogenous Ngn3 gene. For example, the transgenic animal may comprise a. "knock-in" of an Ngn3 gene, such that the host cell genome contains an alteration that results in altered expression (e.g., increased (including ectopic) or decreased expression) of an Ngn3 gene, e.g., by introduction of an additional copy of the target gene, or by operatively inserting a regulatory sequence that provides for enhanced expression of an endogenous copy of the target gene. "Knock-in" transgenics can be transgenic animals having a heterozygous knock-in of the Ngn3 gene or a homozygous knock-in of the Ngn3. "Knock-ins" also encompass conditional knock-ins.

The exogenous gene introduced into the host cell genome to produce a transgenic animal is usually either from a different species than the animal host, or is otherwise altered in its coding or non-coding sequence. The introduced gene may be a wild-type gene, naturally occurring polymorphism, or a genetically manipulated sequence, for example those previously described with deletions, substitutions or insertions in the coding or non-coding regions. The introduced sequence may encode an Ngn3 polypeptide, or may utilize the Ngn3 promoter operably linked to a reporter gene. Where the introduced gene is a coding sequence, it is usually operably linked to a promoter, which may be constitutive or inducible, and other regulatory sequences required for expression in the host animal.

Specific constructs of interest include, but are not limited to, anti-sense Ngn3, or a ribozyme based on an Ngn3 sequence, which will block Ngn3 expression, as well as expression of dominant negative Ngn3 mutations, and over-expression of an Ngn3 gene. A detectable marker, such as lac Z may be introduced into the Ngn3 locus, where upregulation of expression of the corresponding Ngn gene will result in an easily detected change in phenotype. Constructs utilizing a promoter region of the Ngn3 genes in combination with a reporter gene or with the coding region of Ngn3 are also of interest. Constructs having a sequence encoding a truncated or altered (e.g, mutated) Ngn3 are also of interest.

The modified cells or animals are useful in the study of function and regulation of Ngn3 and other proteins involved the pancreatic β-cell developmental pathway. Such modified cells or animals are also useful in, for example, the study of the function and regulation of genes whose expression is affected by Ngn3, as well as the study of the development of insulin-secreting cells in the pancreas. Thus, the transgenic animals of the invention are useful in identifying downstream targets of Ngn3, as such targets may have a role in the phenotypes associated with defects in Ngn3.

Animals may also be used in functional studies, drug screening, etc., e.g. to determine the effect of a candidate drug on islet cell development, on β-cell function and development or on symptoms associated with disease or conditions associated with Ngn3 defects (e.g., on symptoms associated with reduced insulin secretion (e.g., such as that associated with a diabetic syndrome, including Type 2 diabetes). A series of small deletions and/or substitutions may be made in the Ngn3 genes to determine the role of different polypeptide-encoding regions in DNA binding, transcriptional regulation, etc. By providing expression of Ngn3 protein in cells in which it is otherwise not normally produced (e.g., ectopic expression), one can induce changes in cell behavior. These animals are also useful for exploring models of inheritance of disorders associated with diabetes, e.g. dominant v. recessive; relative effects of different alleles and synergistic effects between Ngn3 and other genes elsewhere in the genome.

DNA constructs for homologous recombination will comprise at least a portion of the Ngn3 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. 1990 Methods in Enzymology 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene. Chimeric animals having the modification (normally chimeric males) are mated with wildtype animals to produce heterozygotes, and the heterozygotes mated to produce homozygotes. If the gene alterations cause lethality at some point in development, tissues or organs can be maintained as allogeneic or congenic grafts or transplants, or in in vitro culture.

Investigation of genetic function may utilize non-mammalian models, particularly using those organisms that are biologically and genetically well-characterized, such as *C. elegans, D. melanogaster* and *S. cerevisiae*. For example, transposon (Tc1)insertions in the nematode homolog of an Ngn3 gene or a promoter region of an Ngn3 gene may be made. The Ngn3 gene sequences may be used to knock-out or to complement defined genetic lesions in order to determine the physiological and biochemical pathways involved in function of islet cells. It is well known that human genes can complement mutations in lower eukaryotic models.

Production of Ngn3 Polypeptides

Ngn3-encoding nucleic acid may be employed to synthesize full-length Ngn3 polypeptides or fragments thereof, particularly fragments corresponding to functional domains; DNA binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

As discussed above, the invention encompasses both isolated, naturally-occurring Ngn3 polypeptides, as well as recombinant Ngn3 polypeptides and functional equivalents of such recombinant and/or naturally-occurring Ngn3 polypeptides, e.g., biologically active variants sharing substantial or significant amino acid sequence similarity and/or sequence identity with an Ngn3 amino acid sequence provided herein. Substantial identity, when referring to the Ngn3 polypeptides of the invention are polypeptides having at least about 70%, typically at least about 80% and preferably at least about 90% to about 95% identity to the amino acid sequence of SEQ ID NO:2, or that are encoded by polynucleotides which will hybridize under stringent conditions to a polynucleotide having the nucleotide sequence of SEQ ID NO:1 or SEQ ID NO:3. Percent identity for the polypeptides of the invention is determined using the BLASTP program.

Accordingly, the Ngn3 polynucleotides and polypeptides of this invention include, without limitation, Ngn3 polypeptides and polynucleotides found in primates, rodents, canines, felines, equines, nematodes, yeast and the like, and the natural and non-natural variants thereof.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In many situations, it may be desirable to express the Ngn3 genes in mammaliancells, especially where the encoded polypeptides will benefit from native folding and post-translational modifications. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

The Ngn3 polypeptides can be used for the production of antibodies, where short fragments provide for antibodies specific for the particular polypeptide, and larger fragments or the entire protein allow for the production of antibodies over the surface of the polypeptide. Antibodies may be raised to the wild-type or variant forms of Ngn3. Antibodies may be raised to isolated peptides corresponding to these domains, or to the native protein, e.g. by immunization with cells expressing Ngn3, immunization with liposomes having Ngn3 polypeptides inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E coli, and the heavy and light chains mixed to further enhance the affinity of the antibody. Alternatives to in vivo immunization as a method of raising antibodies include binding to phage "display" libraries, usually in conjunction with in vitro affinity maturation.

Isolation of Ngn3 Allelic Variants and Homologues in Other Species

Other mammalian Ngn3 genes can be identified and their function characterized using the Ngn3 genes used in the present invention. Other Ngn3 genes of interest include, but are not limited to, mamnmalian (e.g., human, rodent (e.g, murine, or rat), bovine, feline, canine, and the like) and non-manimnalian (e.g., chicken, reptile, and the like). Methods for identifying, isolating, sequencing, and characterizing an unknown gene based upon its homology to a known gene sequence are well known in the art (see, e.g., Sambrook et al., Molecular Cloning: A Laboratory Manual, CSH Press 1989.

Drug Screening

The animal models of the invention, as well as methods using the Ngn3 polypeptides in vitro, can- be used to identify candidate agents that affect Ngn3 expression (e.g., by affecting Ngn3 promoter function) or that interact with Ngn3 polypeptides. Agents of interest can include those that enhance, inhibit, regulate, or otherwise affect Ngn3 activity and/or expression. Agents that alter Ngn3 activity and/or expression can be used to, for example, treat or study disorders associated with decreased Ngn3 activity (e.g., diabetes or other pancreatic disorders), and/or to facilitate development of islet cell precursors either in vitro or in vivo. Candidate agents is meant to include synthetic molecules (e.g., small molecule drugs, peptides, or other synthetically produced molecules or compounds, as well as recombinantly produced gene products) as well as naturally-occurring compounds (e.g., polypeptides, endogenous factors present in insulin-producing, hormones, plant extracts, and the like).

Drug Screening Assays

Of particular interest in the present invention is the identification of agents that have activity in affecting Ngn3 expression and/or function. Such agents are candidates for development of treatments for, for example, diabetes or other condition that may be associated with altered Ngn3 activity. Drug screening identifies agents that provide a replacement or enhancement for Ngn3 function in affected cells. Conversely, agents that reverse or inhibit Ngn3 function may provide a means to regulate insulin production. Of particular interest are screening assays for agents that have a low toxicity for human cells.

The term "agent" as used herein describes any molecule, e.g. protein or pharmaceutical, with the capability of altering or mimicking the expression or physiological function of Ngn3. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening of Candidate Agents In Vivo

Agents can be screened for their ability to affect Ngn3 expression or function or to mitigate an undesirable phenotype (e.g., a symptom) associated with an alteration in Ngn3 expression or function. In a preferred embodiment, screening of candidate agents is performed in vivo in a transgenic animal described herein. Transgenic animals suitable for use in screening assays include any transgenic animal having an alteration in Ngn3 expression, and can include transgenic animals having, for example, an exogenous and stably transmitted human Ngn3 gene sequence, a reportergene composed of a (removed human) Ngn3 promoter sequence operably linked to a reporter gene (e.g,. β-galactosidase, CAT, or other gene that can be easily assayed for expression), or a homozygous or heterozygous knockout of an Ngn3 gene. The transgenic animals can be either homozygous or heterozygous for the genetic alteration and, where a sequence is introduced into the animal's genome for expression, may contain multiple copies of the introduced sequence. Where the in vivo screening assay is to identify agents that affect the activity of the Ngn3 promoter, the Ngn3 promoter can be operably linked to a reporter gene (e.g., luciferase) and integrated into the non-human host animal's genome or integrated into the genome of a cultured mammalian cell line.

The candidate agent is administered to a non-human, transgenic animal having altered Ngn3 expression, and the effects of the candidate agent determined. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent hat approaches an upper limit of the amount that can be delivered successfully to the animal), and may include delivery of the agent in different formulation. The agents can be administered singly or can be combined in combinations of two or more, especially where administration of a combination of agents may result in a synergistic effect.

The effect of agent administration upon the transgenic animal can be monitored by assessing Ngn3 function as appropriate (e.g., by examining expression of a reporter or fusion gene), or by assessing a phenotype associated with the Ngn3 expression. For example, where the transgenic animal used in the screen contains a defect in Ngn3 expression (e.g., due to a knock-out of the gene), the effect of the candidate agent can be assessed by determining levels of hormones produced in the mouse relative to the levels produced in the Ngn3 defective transgenic mouse and/or in wildtype mice (e.g, by assessing levels of insulin). Methods for assaying insulin are well known in the art. Where the in vivo screening assay is to identify agents that affect the activity of the Ngn3 promoter and the non-human transgenic animal (or cultured mammalian cell line) comprises an Ngn3 promoter operably linked to a reporter gene, the effects of candidate agents upon Ngn3 promoter activity can be screened by, for example, monitoring the expression from the Ngn3 promoter (through detection of the reporter gene) and correlation of altered Ngn3 promoter activity with islet cell formation. Alternatively or in addition, Ngn3 promoter activity can be assessed by detection (qualitative or quantitative) of Ngn3 mRNA or protein levels. Where the candidate agent affects Ngn3 expression, and/or affects an Ngn3-associated phenotype, in a desired manner, the candidate agent is identified as an agent suitable for use in therapy of an Ngn3-associated disorder and/or to facilitate development of islet precursor cells to mature β-cells either in vivo or in vitro.

Screening of Candidate Agents In Vitro

In addition to screening of agents in Ngn3 transgenic animals, a wide variety of in vitro assays may be used for this purpose, including labeled in vitro protein-protein binding assays, protein-DNA binding assays, electrophoretic mobility shift assays, unmunoassays for protein binding, and the like. For example, by providing for the production of large amounts of Ngn3 protein, one can identify ligands or substrates that bind to, modulate or mimic the action of the proteins. The purified protein may also be used for determination of three-dimensional crystal structure, which can be used for modeling intermolecular interactions, transcriptional regulation, etc.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc that are used to facilitate optimal protein-protein binding, protein-DNA binding, and/or reduce non-specific or background interactions. Reagents that improve the efficiency of the assay; such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic Ngn3 function. For example, candidate agents are added to a cell that lacks functional Ngn3, and screened for the ability Is to reproduce Ngn3 activity in a functional assay.

Many mammalian genes have homologs in yeast and lower animals. The study of such homologs' physiological role and interactions with other proteins in vivo or in vitro can facilitate understanding of biological function. In addition to model systems based on genetic complementation, yeast has been shown to be a powerful tool for studying protein-protein interactions through the two hybrid system described in Chien et al. 1991 Proc. Natl. Acad. Sci. USA 88:9578–9582. Two-hybrid system analysis is of particular interest for exploring transcriptional activation by Ngn3 proteins and to identify cDNAs encoding polypeptides that interact with Ngn3.

Identified Candidate Agents

The compounds having the desired pharmacological activity may be administered in a physiologically acceptable carrier to a host for treatment of a condition attributable to a defect in Ngn3 function (e.g., a disorder associated with reduced insulin levels (e.g., diabetes (Type 1 or Type 2 diabetes, particularly Type 1 diabetes)). The compounds may also be used to enhance Ngn3 function. The therapeutic agents may be administered in a variety of ways, orally, topically, parenterally e.g. subcutaneously, intraperitoneally, by viral infection, intravascularly, etc. Inhaled treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing Agents, wetting and emulsifying Agents, salts for varying the osmotic pressure or buffers for securing an adequate pH value, and skin penetration enhancers can be used as auxiliary agents.

Pharmacogenetics

Pharmacogenetics is the linkage between an individual's genotype and that individual's ability to metabolize or react to a therapeutic agent. Differences in metabolism or target sensitivity can lead to severe toxicity or therapeutic failure by altering the relation between bioactive dose and blood concentration of the drug. In the past few years, numerous studies have established good relationships between polymorphisms in metabolic enzymes or drug targets, and both response and toxicity. These relationships can be used to individualize therapeutic dose administration.

Genotyping of polymorphic alleles is used to evaluate whether an individual will respond well to a particular therapeutic regimen. The polymorphic sequences are also used in drug screening assays, to determine the dose and specificity of a candidate therapeutic agent. A candidate Ngn3 polymorphism is screened with a target therapy to determine whether there is an influence on the effectiveness in treating, for example, diabetes. Drug screening assays are performed as described above. Typically two or more different sequence polymorphisms are tested for response to a therapy. Therapies for diabetes currently include replacement therapy via administration of insulin and administration of drugs that increase insulin secretion (sulfonylureas) and drugs that reduce insulin resistance (such as troglitazone).

Where a particular sequence polymorphism correlates with differential drug effectiveness, diagnostic screening may be performed. Diagnostic methods have been described in detail in a preceding section. The presence of a particular polymorphism is detected, and used to develop an effective therapeutic strategy for the affected individual.

Detection of Ngn3 Associated Disorders

Diagnosis of Ngn3-associated disorders is performed by protein, DNA or RNA sequence and/or hybridization analysis of any convenient sample from a patient, e.g. biopsy material, blood sample, scrapings from cheek, etc. A nucleic acid sample from a patient having a disorder that may be associated with Ngn3, is analyzed for the presence of a predisposing polymorphism in Ngn3. A typical patient genotype will have at least one predisposing mutation on at least one chromosome. The presence of a polymorphic Ngn3 sequence that affects the activity or expression of the gene product, and confers an increased susceptibility to an Ngn3 associated disorder (e.g, hyperglycemia, diabetes, and the like) is considered a predisposing polymorphism. Individuals are screened by analyzing their DNA or mRNA for the presence of a predisposing polymorphism, as compared to sequence from an unaffected individual(s). Specific sequences of interest include, for example, any polymorphism that is associated with a diabetic syndrome, especially with Type 2 diabetes, or is otherwise associated with diabetes, including, but not limited to, insertions, substitutions and deletions in the coding region sequence, intron sequences that affect splicing, or promoter or enhancer sequences that affect the activity and expression of the protein.

Screening may also be based on the functional or antigenic characteristics of the protein. Immunoassays designed to detect predisposing polymorphisms in Ngn3 proteins may be used in screening. Where many diverse mutations lead to a particular disease phenotype, functional protein assays can be effective screening tools.

Biochemical studies may be performed to determine whether a candidate sequence polymorphism in the Ngn3 coding region or control regions is associated with disease. For example, a change in the promoter or enhancer sequence that affects expression of Ngn3 may result in predisposition to diabetes. Expression levels of a candidate variant allele are compared to expression levels of the normal allele by various methods known in the art. Methods for determining promoter or enhancer strength include quantitation of the expressed natural protein; insertion of the variant controlelement into a vector with a reporter gene such as β-galactosidase, luciferase, chloramphenicol acetyltransferase, etc. that provides for convenient quantitation; and the like. The activity of the encoded Ngn3 protein may be determined by comparison with the wild-type protein.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. Cells that express Ngn3 genes, such as, pancreatic cells, may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. 1985 Science 239:487; a review of current techniques may be found in Sambrook, et al. Molecular Cloning: A Laboratory Manual, CSH Press 1989, pp. 14.2–14.33. Amplification may also be used to determine whether a polymorphism is present, by using a primer that is specific for the polymorphism. Alternatively, various methods are known in the art that utilize oligonucleotide ligation as a means of detecting polymorphisms, for examples see Riley et al. 1990 Nucl. Acid Res. 18:2887–2890; and Delahunty et al. 1996 Am. J. Hum. Genet. 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a LI5s number of methods known in the art. The nucleic acid may be sequenced by dideoxy or other methods, and the sequence of bases compared to either a neutral Ngn3 sequence (e.g., an Ngn3 sequence from an unaffected individual). Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The hybridization pattern of a control and variant sequence to an array of oligonucleotide probes immobilized on a solid support, as described in U.S. Pat. No. 5,445,934, or in WO95/35505, may be used as a means of detecting the presence of variant sequences. In one embodiment of the invention, an array of oligonucleotides are provided, where discrete positions on the array are complementary to at least a portion of mRNA or genomic DNA of the Ngn3 locus. Such an array may comprise a series of oligonucleotides, each of which can specifically hybridize to a nucleic acid sequence, e.g,. mRNA, cDNA, genomic DNA, etc. from the Ngn3 locus. Usually such an array will include at least 2 different polymorphic sequences, i.e. polymorphisms located at unique positions within the locus, usually at least about 5, more usually at least about 10, and may include as many as 50 to 100 different polymorphisms. The oligonucleotide sequence on the array will usually be at least about 12 nt in length, may be the length of the provided polymorphic sequences, or may extend into the flanking regions to generate fragments of 100 to 200 nt in length. For examples of arrays, see Hacia et al. 1996 Nature Genetics 14:441–447; Lockhart et al. 1996 Nature Biotechnol. 14:1675–1680; and De Risi et al. 1996 Nature Genetics 14:457–460.

Antibodies specific for Ngn3 polymorphisms may be used in screening immunoassays. A reduction or increase in Ngn3 and/or presence of an Ngn3 disorder associated polymorphism is indicative that the suspected disorder is Ngn3-associated. A sample is taken from a patient suspected of having an Ngn3-associated disorder. Samples, as used herein, include tissue biopsies, biological fluids, organ or tissue culture derived fluids, and fluids extracted from physiological tissues, as well as derivatives and fractions of such fluids. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the absence or presence or altered amounts of normal or abnormal Ngn3 in patient cells suspected of having a predisposing polymorphism in Ngn3. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and Ngn3 in a lysate. Measuring the concentration of Ngn3 binding in a sample or fraction thereof may be accomplished by a variety of specific assays. A conventional sandwich type assay may be used. For example, a sandwich assay may first attach Ngn3-specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of normal and/or abnormal Ngn3 is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind Ngn3 with sufficient specificity such that it can be distinguished from other components present. The second antibodies may be labeled to facilitate direct, or indirect quantification of binding. Examples of labels that permit direct measurement of second receptor binding include radiolabels, such as $^3$H or $^{125}$I, fluorescers, dyes, beads, chemiluminescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for Ngn3 as desired, conveniently using a labeling method as described for the sandwich assay.

Other diagnostic assays of interest are based on the functional properties of Ngn3 proteins. Such assays are particularly useful where a large number of different sequence changes lead to a common phenotype. For example, a functional assay may be based on the transcriptional changes mediated by Ngn3 gene products. Other assays may, for example, detect conformational changes, size changes resulting from insertions, deletions or truncations, or changes in the subcellular localization of Ngn3 proteins.

In a protein truncation test, PCR fragments amplified from the Ngn3 gene or its transcript are used as templates for in vivo transcription/translation reactions to generate protein products. Separation by gel electrophoresis is performed to determine whether the polymorphic gene encodes a truncated protein, where truncations may be associated with a loss of function.

Diagnostic screening may also be performed for polymorphisms that are genetically linked to a predisposition for diabetes, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. 1994 Genomics 24:225–233; Ziegle et al. 1992 Genomics 14:1026–1031; Dib et al., supra.

Microsatellite loci that are useful in the subject methods have the general formula:

$$U(R)_n U',$$

where U and U' are non-repetitive flanking sequences that uniquely identify the particular locus, R is a repeat motif, and n is the number of repeats. The repeat motif is at least 2 nucleotides in length, up to 7, usually 2–4 nucleotides in length. Repeats can be simple or complex. The flanking sequences U and U' uniquely identify the microsatellite locus within the human genome. U and U' are at least about 18 nucleotides in length, and may extend several hundred bases up to about 1 kb on either side of the repeat. Within U and U', sequences are selected for amplification primers. The exact composition of the primer sequences are not critical to the invention, but they must hybridize to the flanking sequences U and U', respectively, under stringent conditions. Criteria for selection of amplification primers are as previously discussed. To maximize the resolution of size differences at the locus, it is preferable to chose a primer sequence that is close to the repeat sequence, such that the total amplification product is between 100–500 nucleotides in length.

The number of repeats at a specific locus, n, is polymorphic in a population, thereby generating individual differences in the length of DNA that lies between the amplification primers. The number will vary from at least 1 repeat to as many as about 100 repeats or more.

The primers are used to amplify the region of genomic DNA that contains the repeats. Conveniently, a detectable label will be included in the amplification reaction, as previously described. Multiplex amplification may be performed in which several sets of primers are combined in the same reaction tube. This is particularly advantageous when limited amounts of sample DNA are available for analysis. Conveniently, each of the sets of primers is labeled with a different fluorochrome.

After amplification, the products are size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. 1991 Science 254:59–74. The automated sequencer is particularly useful with multiplex amplification or pooled products of separate PCR reactions. Capillary electrophoresis may also be used for fractionation. A review of capillary electrophoresis may be found in Landers, et al. 1993 Bio-Techniques 14:98–111. The size of the amplification product is proportional to the number of repeats (n) that are present at the locus specified by the primers. The size will be polymorphic in the population, and is therefore an allelic marker for that locus.

Therapeutic Uses of Ngn3-Encoding Nucleic Acid

Ngn3-encoding nucleic acid can be introduced into a cell to accomplish transformation of the cell, preferably stable transformation, and the transformed cell subsequently implanted into a subject having a disorder characterized by a deficiency in insulin (e.g., an Ngn3-associated disorder), depending upon the tissue into which the transformed cell is implanted. Preferably, the host cell to be transformed and implanted in the subject is derived from the individual who will receive the transplant (e.g., to provide an autologous transplant). Where the transformed cells are to be inserted into individual (e.g., into the pancreas, liver, abdominal cavity, etc.), the cells into which the nucleic acid is introduced are preferably stem cells capable of developing into βcells within the pancreatic tissue environment, e.g., stem cells derived from pancreatic tissue, gastrointestinal tissue, or cells capable of expression of insulin upon expression of the Ngn3-encoding nucleic acid.

For example, in a subject having Type 1 diabetes, gastrointestinal stem cells can be isolated from the affected subject, the cells transformed with Ngn3-encoding DNA, and the transformed cells implanted in the affected subject to provide for insulin production, or the transformed cells cultured so as to facilitate development of the cells into insulin-producing β-cells.

Introduction of the Ngn3-encoding nucleic acid into the cell can be accomplished according to methods well known in the art (e.g., through use of electroporation, microinjection, lipofection infection with a recombinant (preferably replication-deficient) virus, and other means well known in the art). Preferably, the Ngn3-encoding nucleic acid is operably linked to a promoter that facilitates a desired level of Ngn3 polypeptide expression (e.g., a promoter derived from CMV, SV40, adenovirus, or a tissue-specific or cell type-specific promoter). Transformed cells containing the Ngn3-encoding nucleic acid can be selected and/or enriched via, for example, expression of a selectable marker gene present in the Ngn3-encoding construct or that is present on a plasmid that is co-transfected with the Ngn3-encoding construct. Typically selectable markers provide for resistance -to antibiotics such as tetracycline, hygromycin, neomycin, and the like. Other markers can include thymidine kinase and the like.

The ability of the transformed cells to express the Ngn3-encoding nucleic acid can be assessed by various methods known in the art. For example, Ngn3 expression can be examined by Northern blot to detect mRNA which hybridizes with a DNA probe derived from the relevant gene. Those cells that express the desired gene can be further isolated and expanded in in vitro culture using methods well known in the art. The host cells selected for transformation with Ngn3-encoding DNA will vary with the purpose of the ex vivo therapy (e.g., insulin production), the site of implantation of the cells, and other factors that will vary with a variety of factors that will be appreciated by the ordinarily skilled artisan.

Methods for engineering a host cell for expression of a desired gene product(s) and implantation or transplantion of the engineered cells (e.g., ex vivo therapy) are known in the art (see, e.g., Gilbert et al. 1993 "Cell transplantation of genetically altered cells on biodegradable polymer scaffolds in syngeneic rats," Transplantation 56:423–427). For expression of a desired gene in exogenous or autologous cells and implantation of the cells (e.g., islet cells) into pancreas, see, e.g., Docherty 1997 "Gene therapy for diabetes mellitus," Clin Sci (Colch) 92:321–330; Hegre et al. 1976 "Transplantation of islet tissue in the rat," Acta Endocrinol Suppl (Copenh) 205:257–281; Sandler et al. 1997 "Assessment of insulin secretion in vitro from microencapsulated fetal porcine islet-like cell clusters and rat, mouse, and human pancreatic islets," Transplantation 63:1712–1718; Calafiore 1997 "Perspectives in pancreatic and islet cell transplantation for the therapy of IDDM," Diabetes Care 20:889–896; Kenyon et al. 1996 "Islet cell transplantation: beyond the paradigms," Diabetes Metab Rev 12:361–372; Sandler; Chick et al. 1977 Science "Artificial pancreas using living beta cells: effects on glucose homeostasis in diabetic rats," 197:780–782.

After expansion of the transformed cells in vitro, the cells are implanted into the mammalian subject, preferably into the tissue from which the cells were originally derived, by methods well known in the art. The number of cells implanted is a number of cells sufficient to provide for expression of levels of Ngn3 sufficient to provide for enhanced levels of insulin. The number cells to be transplanted can be determined based upon such factors as the levels of polypeptide expression achieved in vitro, and/or the number of cells that survive implantation. Preferably the cells are implanted in an area of dense vascularization, and in a manner that minimizes evidence of surgery in the subject. The engraftment of the implant of transformed cells is monitored by examining the mammalian subject for classic signs of graft rejection, i.e., inflammation and/or exfoliation at the site of implantation, and fever.

Alternatively, Ngn3-encoding nucleic acid can be delivered directly to an affected subject to provide for Ngn3 expression in a target cell (e.g., a pancreatic cell, gut cell, liver cell, or other organ cell capable of expressing Ngn3 and providing production of insulin), thereby promoting development of the cell into an insulin-producing cell (e.g., in pancreas) or to cure a defect in Ngn3 expression in the subject. Methods for in vivo delivery of a nucleic acid of interest for expression in a target cell are known in the art. For example, in vivo methods of gene delivery normally employ either a biological means of introducing the DNA into the target cells (e.g., a virus containing the DNA of interest) or a mechanical means to introduce the DNA into the target cells (e.g., direct injection of DNA into the cells, liposome fusion, pneumatic injection using a "gene gun," or introduction of the DNA via a duct of the pancreas). For other methods of introduction of a DNA of interest into a cell in vivo, also see Bartlett et al. 1997 "Use of biolistic particle accelerator to introduce genes into isolated islets of Langerhans," Transplant Proc 29:2201–2202; Furth 1997 "Gene transfer by biolistic process," Mol Biotechnol 7:139–143; Gainer et al. 1996 "Successful biolistic transformation of mouse pancreatic islets while preserving cellular function," Transplantation 61:1567–1571; Docherty 1997 "Gene therapy for diabetes mellitus," Clin Sci (Colch) 92:321–330; Maeda et al. 1994 "Gastroenterology 1994 "Adenovirus-mediated transfer of human lipase complementary DNA to the gallbladder," 106:1638–1644.

The amount of DNA and/or the number of infectious viral particles effective to infect the targeted tissue, transform a sufficient number of cells and provide for production of a desired level of insulin can be readily determined based upon such factors as the efficiency of the transformation in vitro and the susceptibility of the targeted secretory gland cells to transformation. For example, the amount of DNA injected into the pancreas of a human is, for example, generally from about 1 $\mu$g to 750 mg, preferably from about 500 $\mu$g to 500 mg, more preferably from about 10 mg to 200 mg, most preferably about 100 mg. Generally, the amounts of DNA can be extrapolated from the amounts of DNA effective for delivery and expression of the desired gene in an animal model. For example, the amount of DNA for delivery in a human is roughly 100 times the amount of DNA effective in a rat.

Regardless of whether the Ngn3-encoding DNA is introduced in vivo or ex vivo, the DNA (or cells expressing the DNA) can be administered in combination with other genes and other agents. In addition, Ngn3-encoding DNA (or recombinant cells expressing Ngn3 DNA) can be used therapeutically for disorders associated with, for example, a decrease in insulin production, but which are not associated with an alteration in Ngn3 function per se. For example, an increase in Ngn3 may cause an increase in the number of mature $\beta$cells, and thus an increase in insulin production, in an individual that has decreased insulin production from some other cause not related to function of Ngn3.

Identification of Islet Cell Precursors and Development of $\beta$-Cells Using Ngn3

As described in more detail in the Examples below, the temporal and spatial pattern of Ngn3 expression indicates that Ngn3 can be used as a marker for islet cell precursors. This feature of Ngn3 expression can be exploited to provide compositions and methods to identify and isolate islet cell precursors. For example, pancreatic tissue can be obtained from a subject, and a single cell suspension obtained from the tissue. The single cell cultures can then be expanded in culture, and representative cells from the single cell cultures analyzed for Ngn3 expression. Ngn3 expression can be analyzed by, for example, detection of Ngn3-encoding mRNA (e.g., by PCR amplification using a probe derived from an Ngn3-encoding sequence) or by detection of the Ngn3 polypeptide in cell lysates using an anti-Ngn3 antibody. Cells that express Ngn3 are identified as being islet cell precursors. The cells of the corresponding culture could then be expanded and/or used to derive mature $\beta$-cells in culture, and the mature $\beta$-cells implanted into the subject, e.g., either into the same subject from whom the cells were initially obtained or into a different subject.

Ngn3 is also useful for monitoring development of islet cell precursors into mature $\beta$-cells. In short, Ngn3 expression can be monitored in an in vitro culture to determine when the cells become mature $\beta$-cells. For example, cells that express Ngn3 are at an earlier stage of $\beta$-cell development. Once Ngn3 expression decreases or becomes substantially undetectable, the cell can be identified as having developed into a mature $\beta$-cell. The cells can be screened for other markers of islet cell development, as well as for insulin production.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Detection of Ngn3 Expression in Murine Pancreas

Members of the basic helix-loop-helix (bHLH) family of transcription factors regulate growth and differentiation of numerous cell types. Insulin gene expression is activated by a heterodimeric complex of two bHLH proteins: a ubiquitously expressed (class A) protein and a cell-type-specific (class B) partner, BETA2/neuroD1. BETA2/neuroD1 is also important for β-cell development. The targeted disruption of the BETA2/neuroD1 gene in mice leads to a marked reduction of the β-cell mass at birth due to increased apoptosis of islet cells late in fetal development. There is no apparent defect, however, in β-cell formation or insulin gene expression, despite the postulated importance Of this factor in β-cell differentiation.

Assuming that this modest phenotype reflected the redundant expression of closely related class B bHLH proteins in the endocrine pancreas, the inventors searched for additional members of the family by reverse transcriptase-polymerase chain reaction (RT-PCR) using degenerate oligonucleotides primers based on conserved amino acid sequences in the bHLH domain of the class B bHLH proteins (Sommer et al. 1996 *Mol. Cell. Neurosci.* 8:221). PCR analysis revealed that pancreatic endocrine cell lines and isolated adult islets not only express neuroD1, but also several other members of the family of neural class B bHLH genes as well, including mash1, neuroD2 and 4 and neurogenins (ngn) 1, 2 and 3. This remarkable degree of redundancy could compensate for the loss of BETA2/neuroD1 in mice. The two most commonly amplified sequences encoded neuroD4 and Ngn3, but in situ hybridization studies in mouse pancreas showed highest expression of neuroD1 and Ngn3. These results were confirmed by immunohistochemistry.

Ngn3 is detected earliest at embryonic day 11.5 (e11.5) in the mouse, increases to a maximum at e15.5 and decreases at e18.5, with no staining seen in the adult pancreas. Ngn3 is detected in the nuclei of scattered ductal cells and peri-ductal cells, and there was no co-staining with any of the four islet hormones (insulin, glucagon, somatostatin and pancreatic polypeptide). This temporal and spatial pattern of expression implicated Ngn3 as a marker for islet cell precursors. Nkx6.1, a specific marker for future beta-cells, was expressed in 10–20% of the Ngn3 positive cells, further supporting the use of Ngn3 as a marker for islet cell precursors. The peak of Ngn3 expression at e15.5 also corresponds with the peak of new beta-cell formation in the fetus. Our data supports a model in which Ngn3 acts upstream of BETA2/neuroD1 and other islet differentiation factors, marking islet cell precursors, but switching off prior to final differentiation.

Example 2

Isolation and Sequencing of a Human Ngn3' Polypeptide-Encoding Polynucleotide A probe derived from a cloned fragment of the murine Ngn3 gene (Somimer et al., supra) was used to screen a human genomic library. This screen resulted in the isolation of the genomic sequence provided as SEQ ID NO:1 in the sequence listing. Based on mapping of the murine start site using 5' RACE of mouse fetal pancreatic RNA, the transcriptional start site in the human Ngn3-encoding sequence is at nucleotide residue 2643. The coding sequence is between nucleotide residues 3022–3663, with a stop site at 3664–3666. No introns are within the 5' untranslated region (UTR) or the coding sequence of SEQ ID NO:1.

The promoter of Ngn3 is of interest, particularly given that is it exceptionally well-conserved between mouse, rat, and human. Given the role of Ngn3 in pancreatic and islet cell development, the Ngn3 promoter is likely key to determining the number of islet cells in the mature pancreas. The regulatory region corresponding to the human Ngn3 promoter comprises sequences up to approximately 500 bp upstream of the transcription start site within the human Ngn3 promoter (e.g., from about 2144 to the transcriptional start site at 2643).

FISH was used to identify the location of Ngn3 on the human chromosome at 10q22.1–22.2.

Example 3

Isolation and Sequencing of a Murine Ngn3 Polypeptide-Encoding Polynucleotide and Promoter The full-length murine Ngn3 sequence and its 5' flanking sequences, which included the murine Ngn3 promoter, were obtained by sequencing a previously obtained mouse genomic DNA fragment (Sommer, et al., supra). The murine Ngn3 sequence is provided in the Sequence Listing as SEQ ID NO:3, with the encoded polypeptide provided as SEQ ID NO:4. The transcriptional start site was determined using the 5' RACE method and confirmed using Rnase protection with RNA from fetal mouse pancreas, and iis at nucleotide residue 719; the coding sequence for murine Ngn3 begins at nucleotide residue 1093. The promoter comprises a region approximately 500 bp upstream of the transcription start site.

The invention now being fully described, it will be apparent to one of ordinary skill in the art that many changes and modifications can be made thereto without departing from the spirit or scope of the appended claims.

---

What is claimed is:

1. An isolated polynucleotide or full complement thereof, wherein said polynucleotide encodes a polypeptide having the amino acid sequence set forth in SEQ ID NO:2.

2. An isolated polynucleotide or full complement thereof, comprising a polynucleotide sequence of nucleotides 3022–3663 of SEQ ID NO:1.

3. A recombinant expression vector comprising the polynucleotide of claim 2 or 1.

4. An isolated recombinant host cell comprising the polynucleotide of claims 2 or 1.

5. A method for producing a polypeptide, the method comprising the steps of:

a) culturing a recombinant host cell containing the polynucleotide of claims 2 or 1, under conditions suitable for the expression of an encoded polypeptide; and b) recovering the polypeptide from the host cell culture.

* * * * *